United States Patent
Taniguchi et al.

(10) Patent No.: US 8,871,427 B2
(45) Date of Patent: Oct. 28, 2014

(54) POSITIVE RESIST COMPOSITION AND PATTERNING PROCESS

(75) Inventors: Ryosuke Taniguchi, Jyoetsu (JP); Akihiro Seki, Jyoetsu (JP); Kenji Funatsu, Jyoetsu (JP); Katsuhiro Kobayashi, Jyoetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 13/526,057

(22) Filed: Jun. 18, 2012

(65) Prior Publication Data
US 2013/0045444 A1 Feb. 21, 2013

(30) Foreign Application Priority Data

Aug. 17, 2011 (JP) ................................. 2011-178205

(51) Int. Cl.
| | |
|---|---|
| G03F 7/004 | (2006.01) |
| G03F 7/20 | (2006.01) |
| H01L 21/027 | (2006.01) |
| C07C 381/12 | (2006.01) |
| G03F 7/11 | (2006.01) |
| C08F 220/34 | (2006.01) |
| G03F 7/039 | (2006.01) |
| G03F 7/32 | (2006.01) |
| C08F 220/36 | (2006.01) |

(52) U.S. Cl.
CPC ............ *G03F 7/0397* (2013.01); *G03F 7/20* (2013.01); *H01L 21/0273* (2013.01); *C07C 381/12* (2013.01); *G03F 7/11* (2013.01); *C08F 220/34* (2013.01); *G03F 7/2041* (2013.01); *G03F 7/32* (2013.01); *C08F 220/36* (2013.01); *Y10S 430/114* (2013.01); *Y10S 430/115* (2013.01)
USPC ......... 430/270.1; 430/322; 430/396; 430/913; 430/914

(58) Field of Classification Search
CPC ..... G03F 7/004; G03F 7/0395; G03F 7/0397; G03F 7/2041; G03F 7/32; C07C 381/12; H01L 21/0273; C08F 220/34; C08F 220/36
USPC ............................... 430/270.1–326
See application file for complete search history.

(56) References Cited

U.S. PATENT DOCUMENTS 8,293,449 B2 * 10/2012 Iwai et al. ............... 430/270.1
8,426,108 B2 * 4/2013 Masunaga et al. ....... 430/270.1
(Continued)

FOREIGN PATENT DOCUMENTS

JP A-2001-166476 6/2001
JP A-2008-111103 5/2008
(Continued)

OTHER PUBLICATIONS

Owa, Soichi et al., *Immersion lithography; its potential performance and issues*, Optical Microlithography XVI, Proceedings of SPIE, vol. 5040, 2003, pp. 724-733.
(Continued)

*Primary Examiner* — Amanda C Walke
(74) *Attorney, Agent, or Firm* — Oliff PLC

(57) ABSTRACT

There is disclosed a positive resist composition comprising (A) a resin having repeating units shown by the following general formulae (1) and (2) as repeating units that contain acid labile groups and being capable of increasing its alkaline solubility by an acid, (B) a photoacid generator, (C) a compound shown by the following general formula (3), and (D) a solvent. There can be a positive resist composition having high resolution, and at the same time giving an excellent pattern profile; and a patterning process in which an immersion lithography is carried out using a formed top coat.

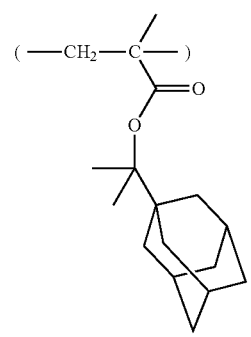

(1)

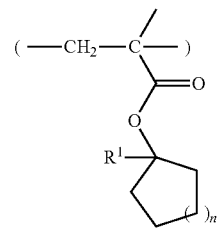

(2)

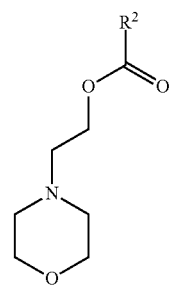

(3)

16 Claims, No Drawings

(56) References Cited

U.S. PATENT DOCUMENTS

| | | | |
|---|---|---|---|
| 8,470,511 B2 * | 6/2013 | Masunaga et al. | 430/270.1 |
| 8,609,319 B2 * | 12/2013 | Kimura et al. | 430/270.1 |
| 8,614,048 B2 * | 12/2013 | Ichikawa et al. | 430/270.1 |
| 2008/0090172 A1 | 4/2008 | Hatakeyama et al. | |
| 2008/0118860 A1 | 5/2008 | Harada et al. | |
| 2008/0274421 A1 * | 11/2008 | Tsubaki | 430/270.1 |
| 2009/0011365 A1 * | 1/2009 | Kobayashi et al. | 430/284.1 |
| 2009/0061358 A1 * | 3/2009 | Ohashi et al. | 430/286.1 |
| 2009/0186297 A1 * | 7/2009 | Ohsawa et al. | 430/270.1 |
| 2009/0208886 A1 | 8/2009 | Takemura et al. | |
| 2009/0274978 A1 | 11/2009 | Ohashi et al. | |
| 2011/0033803 A1 | 2/2011 | Hatakeyama et al. | |
| 2011/0091812 A1 | 4/2011 | Hatakeyama et al. | |

FOREIGN PATENT DOCUMENTS

| | | |
|---|---|---|
| JP | A-2008-122932 | 5/2008 |
| JP | A-2009-217250 | 9/2009 |
| JP | A-2009-269953 | 11/2009 |
| JP | A-2011-053666 | 3/2011 |
| JP | A-2011-095662 | 5/2011 |
| JP | A-2011-102974 | 5/2011 |

OTHER PUBLICATIONS

Nov. 26, 2013 Notification of Reasons for Refusal issued in Japanese Application No. 2011-178205 with partial English-language translation.

* cited by examiner

POSITIVE RESIST COMPOSITION AND PATTERNING PROCESS

BACKGROUND OF THE INVENTION

1. Field of the Invention

The present invention relates to a positive resist composition and a patterning process using the same.

2. Description of the Related Art

In an ArF immersion lithography, a proposal is made to impregnate water between a projector lens and a wafer. A refractive index of water at 193 nm is 1.44, and therefore a pattern formation is possible even if a lens with a numerical aperture (NA) of 1.0 or more is used, and moreover, theoretically NA may be increased to near 1.35. A miniaturization to a level of 45 nm or lower becomes possible by combination of a lens having NA of 1.2 or more and a super-resolution technology (Proc. SPIE Vol. 5040 p 724).

In the immersion lithography, various problems have been pointed out due to presence of water on a resist film. Namely, the problems include a pattern profile change and contamination of a projection lens of an exposure apparatus, due to leaching of a photoacid generator in the resist composition; an acid generated by photoirradiation; an amine compound added to the resist film as a quencher; and the like, to water which is in contact with the resist film.

In order to avoid these problems, a measure has been taken to form a top coat on a resist film to suppress the leaching. However, although the leaching could be suppressed by the top coat, there appeared problems of deterioration in pattern profile and resolution. As to the pattern profile, there was a problem of causing a round head, namely, a top loss.

On top of that, as the requirement of higher resolution increases, improvement in various lithography performances is wanted. In particular, in order to improve a process margin and so on during patterning, improvement of characteristics in Depth of Focus (DOF) is wanted.

SUMMARY OF THE INVENTION

The present invention was made in view of the above situation, and its object is to provide; a positive resist composition having high resolution, in particular excellent characteristics in Depth of Focus (DOF), and at the same time giving an excellent pattern profile; and a patterning process in which an immersion lithography is carried out using a formed top coat whereby photo-exposure is done through water.

In order to solve the problems mentioned above, the present invention provides a positive resist composition comprising (A) a resin having repeating units shown by the following general formulae (1) and (2) as repeating units that contain acid labile groups and being capable of increasing its alkaline solubility by an acid, (B) a photoacid generator, (C) a compound shown by the following general formula (3), and (D) a solvent,

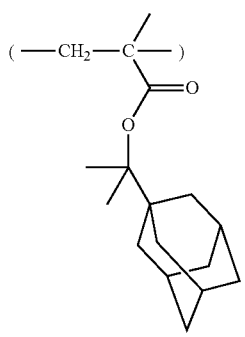

(1)

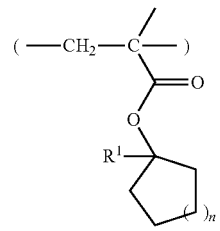

(2)

wherein $R^1$ represents a linear or a branched alkyl group having 1 to 10 carbon atoms and "n" represents an integer of 1 to 3;

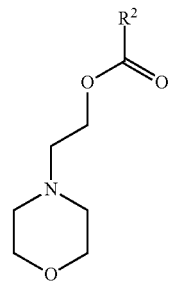

(3)

wherein $R^2$ represents a linear or a branched alkyl group having 10 to 20 carbon atoms and optionally containing an ether bond and an ester bond.

When the positive resist composition of the present invention as mentioned above is used, excellent resolution can be obtained; especially DOF characteristics of pulling performance (trench pattern) and leaving performance (isolated pattern) can be improved. In addition, a resist film capable of giving an excellent pattern profile can be formed.

In addition, it is preferable that the resin of the component (A) contain further a repeating unit shown by the following general formula (4) and/or a repeating unit shown by the following general formula (5).

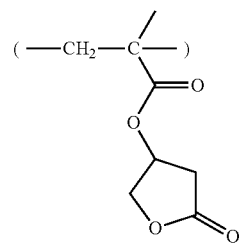

(4)

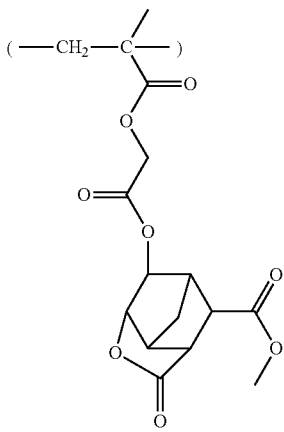

(5)

As mentioned above, when the resin of the component (A) of the present invention further contains the repeating unit shown by the general formula (4) and/or the repeating unit shown by the general formula (5) (these units contain lactone rings), a resist film having excellent adhesion property can be obtained so that a resist pattern having a more desirable profile can be obtained.

In addition, it is preferable that the resin of the component (A) contain further a repeating unit shown by the following general formula (6).

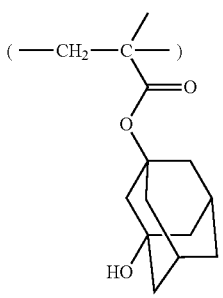

(6)

As mentioned above, when the resin of the component (A) further contains the repeating unit shown by the general formula (6) (this unit contains a hydroxyl group), acid diffusion can be suppressed so that excellent resolution can be obtained.

In addition, it is preferable that amount of the component (C) be 0.5 to 10 parts by mass relative to 100 parts by mass of the resin of the component (A).

When the component (C) is contained therein with the amount as mentioned above, effects of the present invention can be fully expressed; and thus, this amount is preferable.

In addition, the present invention provides a patterning process, wherein the process comprises:

a step of applying on a substrate a positive resist composition comprising (A) a resin having repeating units shown by the following general formulae (1) and (2) as repeating units that contain acid labile groups and being capable of increasing its alkaline solubility by an acid, (B) a photoacid generator, (C) a compound shown by the following general formula (3), and (D) a solvent, and then heating the composition to form a photoresist film, a step of forming a top coat on the photoresist film, a step of immersion exposure thereof through water by using a high energy beam having a wavelength ranging from 180 to 250 nm, and a step of development by using an alkaline developer.

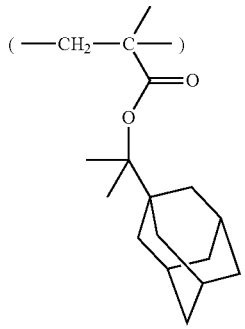

(1)

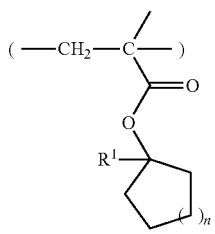

(2)

wherein $R^1$ represents a linear or a branched alkyl group having 1 to 10 carbon atoms and "n" represents an integer of 1 to 3;

Accordingly, when the patterning process of the present invention using the positive resist composition as mentioned above is used, deterioration of pattern profile and resolution that likely occur in a conventional immersion exposure using a top coat can be suppressed. Specifically, a pattern profile having high rectangularity may be obtained; and in addition, excellent Depth of Focus (DOF), specifically excellent DOF characteristics in a trench pattern and an isolated pattern, can be obtained.

In addition, it is preferable that the resin of the component (A) contain further a repeating unit shown by the following general formula (4) and/or a repeating unit shown by the following general formula (5).

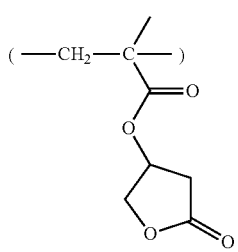

(4)

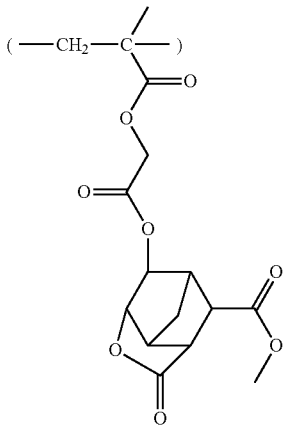
(5)

As mentioned above, if the resin of the component (A) used in the present invention further contains the repeating unit shown by the general formula (4) and/or the repeating unit shown by the general formula (5) (these units contain lactone rings), a resist film having excellent adhesion property can be obtained so that a resist pattern having a more desirable profile can be obtained.

In addition, it is preferable that the resin of the component (A) contain further a repeating unit shown by the following general formula (6).

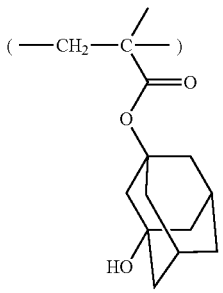
(6)

As mentioned above, if the resin of the component (A) of the present invention further contains the repeating unit shown by the general formula (6) (this unit contains a hydroxyl group), acid diffusion can be suppressed so that excellent resolution can be obtained.

In addition, it is preferable that amount of the component (C) be 0.5 to 10 parts by mass relative to 100 parts by mass of the resin of the component (A).

If the component (C) is contained therein with the amount as mentioned above, effects of the present invention can be fully expressed; and thus, this amount is preferable.

The positive resist composition of the present invention has excellent resolution; especially excellent DOF characteristics in any of an isolated pattern and a trench pattern can be obtained. In addition, in the present invention, an effect to form a resist pattern having an excellent profile can be obtained. In particular, a positive resist composition like this is very useful in an immersion lithography using a formed top coat whereby photo-exposure is done through water. In addition, if the patterning process of the present invention is used, deterioration of pattern profile and resolution that likely occur in a conventional immersion exposure using a top coat can be suppressed. Specifically, a pattern profile having high rectangularity can be obtained; and in addition, excellent Depth of Focus (DOF), specifically excellent DOF characteristics in a trench pattern and an isolated pattern, can be obtained.

DETAILED DESCRIPTION OF THE PREFERRED EMBODIMENTS

As mentioned above, a positive resist composition capable of suppressing deterioration of pattern profile and resolution, especially suppressing deterioration of DOF characteristics, without causing a problem such as, for example, a top loss even if a top coat is formed, has been wanted.

Inventors of the present invention carried out an extensive investigation to achieve the object as mentioned above; and as a result, they found that a positive resist composition comprising—(A) a resin having a repeating unit whose carboxylic acid group (this is a soluble group) was protected by an acid labile group having an adamantane ring (this is a repeating unit shown by the general formula (1) described later) and a repeating unit whose carboxylic acid group (this is a soluble group) was protected by an acid labile group having a specific monocyclic structure (this is a repeating unit shown by the general formula (2) described later), (C) a compound shown by the general formula (3) described later, (B) a photoacid generator, and (D) a solvent—gave excellent resolution and rectangularity in a pattern profile thereby extremely useful as a resist composition for fine microprocessing; and based on this finding, the present invention could be accomplished.

Especially, it was found that the positive resist composition of the present invention gave excellent DOF characteristics in any of an isolated pattern and a trench pattern. Meanwhile, "DOF" means a range of depth of focus in which a resist pattern can be formed within an intended range of a size difference relative to the target size when photo-exposure is conducted with moving a focal point up and down with the same exposure dose, that is, a range in which a resist pattern coincident with a mask pattern can be obtained; and thus, larger DOF is more preferable.

The positive resist composition of the present invention contains, as the component (A), a resin having repeating units shown by the following general formulae (1) and (2) as repeating units that contain acid labile groups and being capable of increasing its alkaline solubility by an acid,

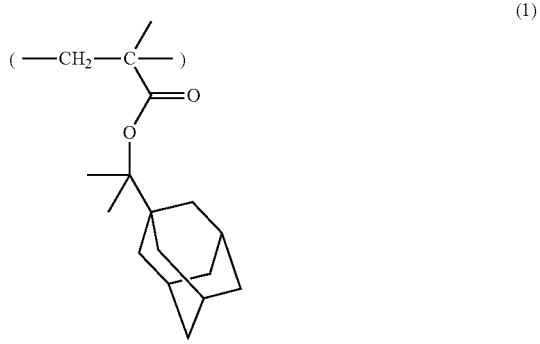
(1)

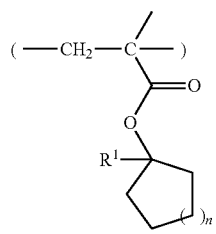
(2)

wherein R¹ represents a linear or a branched alkyl group having 1 to 10 carbon atoms and "n" represents an integer of 1 to 3,

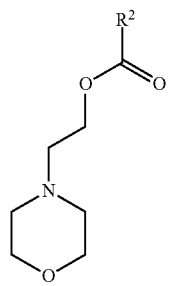
(3)

wherein R² represents a linear or a branched alkyl group having 10 to 20 carbon atoms and optionally containing an ether bond and an ester bond.

The repeating unit containing an acid labile group shown by the general formula (1) is a repeating unit whose carboxylic acid group (this is a soluble group) is protected by an acid labile group having an adamantane ring. When this repeating unit is introduced as the constituent element into the resin of the component (A) capable of increasing its alkaline solubility by an acid, high resolution can be obtained.

The repeating unit containing an acid labile group shown by the general formula (2) is a repeating unit whose carboxylic acid group (this is a soluble group) is protected by an acid labile group having a specific monocyclic structure. When this repeating unit is introduced as the constituent element into the resin of the component (A) capable of increasing its alkaline solubility by an acid, a lipophilicity can be reduced and at the same time resist dissolution contrast can be enhanced; and thus, by combining this with the component (C) described later, a positive resist composition capable of giving excellent resolution, especially excellent DOF characteristics, and an excellent pattern profile can be obtained.

Among the repeating units shown by the general formula (2), repeating units shown below are particularly preferable.

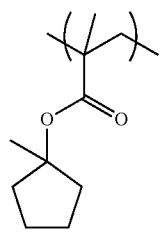 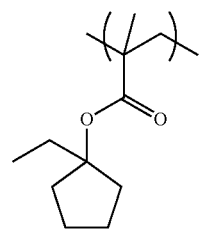

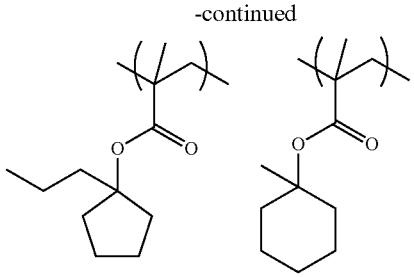

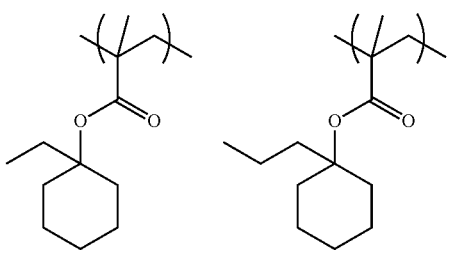

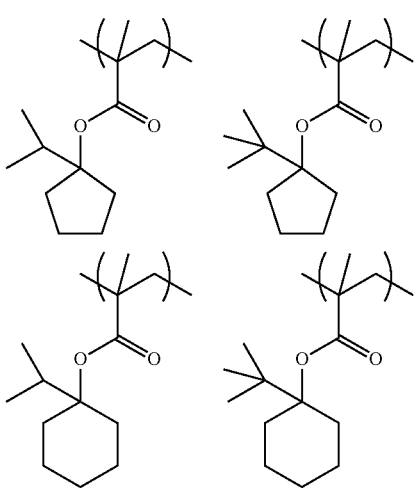

It is preferable that the resin of the component (A) of the positive resist composition of the present invention contain further a repeating unit containing a hydroxyl group and/or a lactone ring in addition to the repeating units shown by the general formulae (1) and (2). Accordingly, when the resin of the component (A) contains a repeating unit containing a hydroxyl group or a lactone ring, satisfactory rectangularity can be obtained even in a fine pattern.

Illustrative example of the repeating unit having a lactone ring as an adhesive group includes the followings.

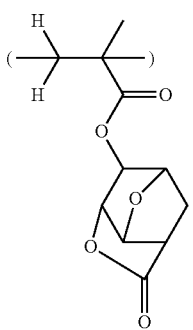 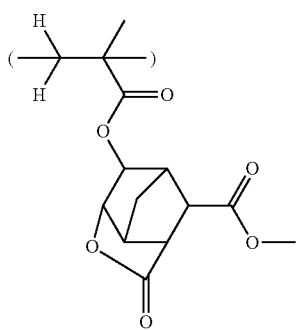

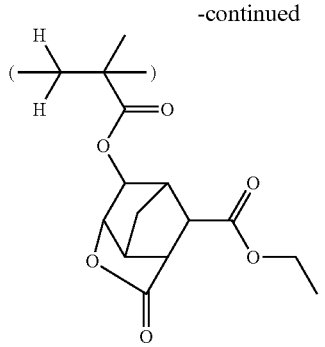
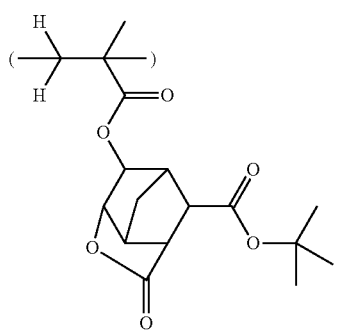
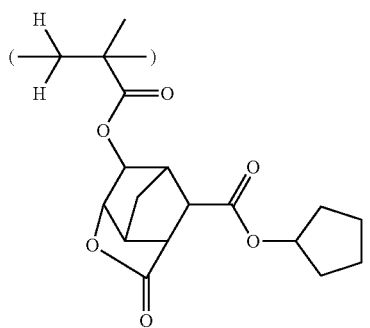
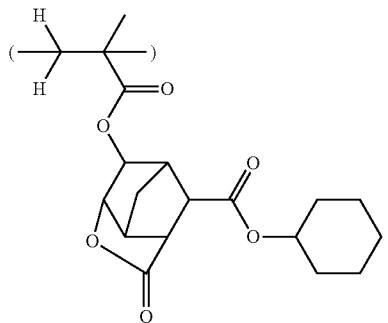
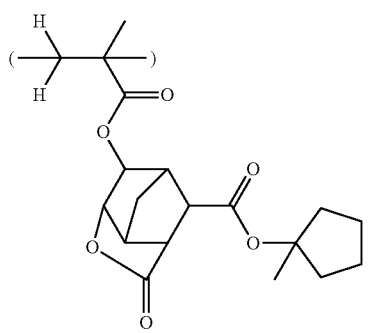
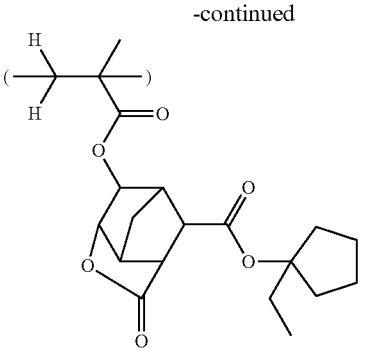
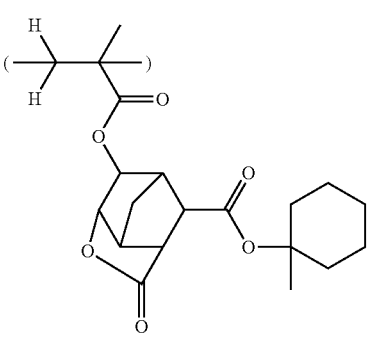
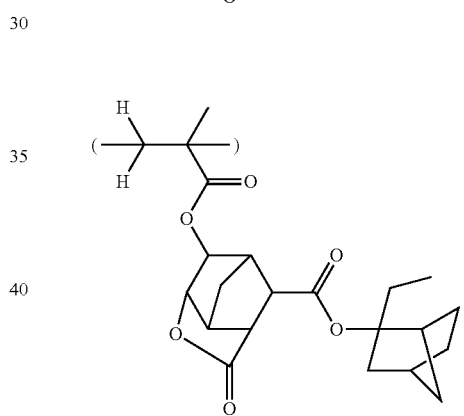
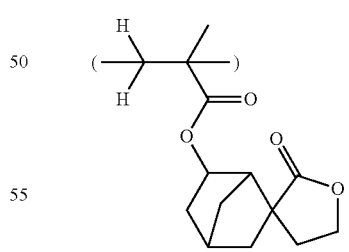
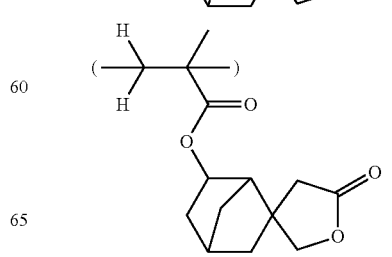

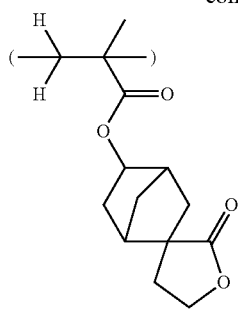
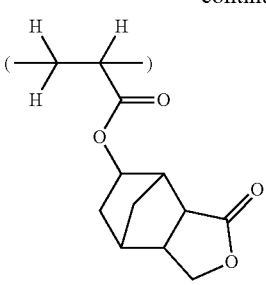
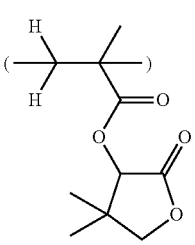
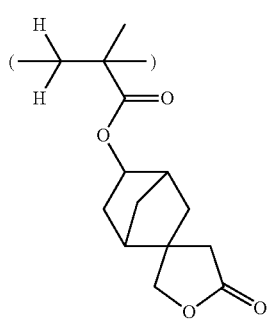
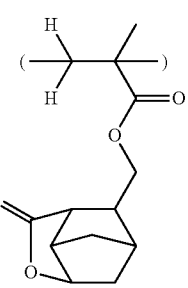
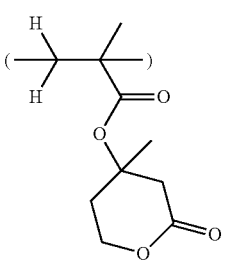
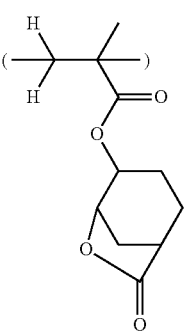
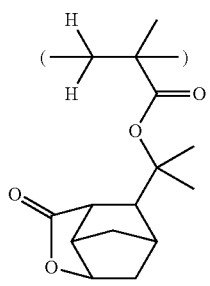
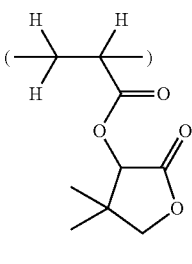
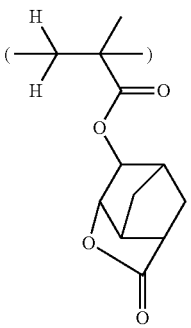
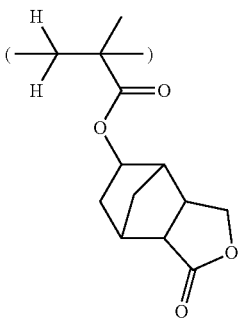
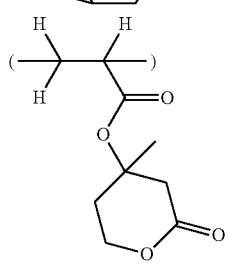
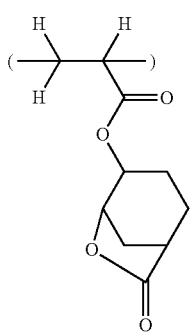
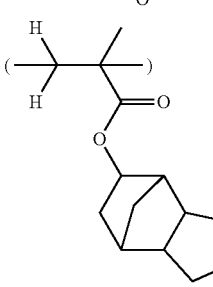
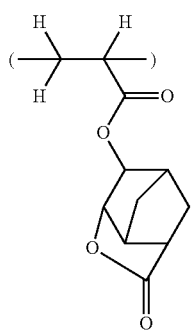
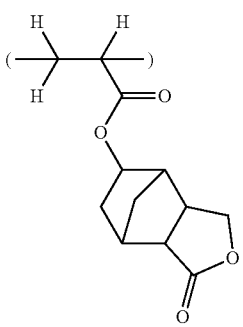
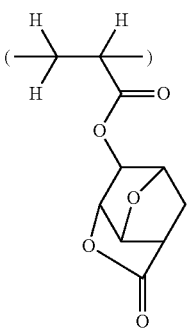
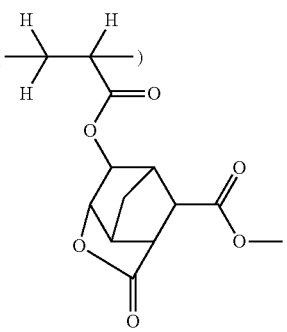

-continued
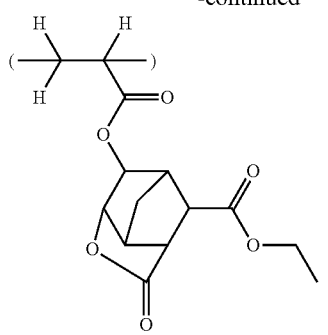
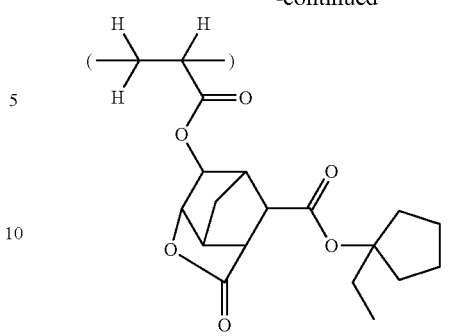
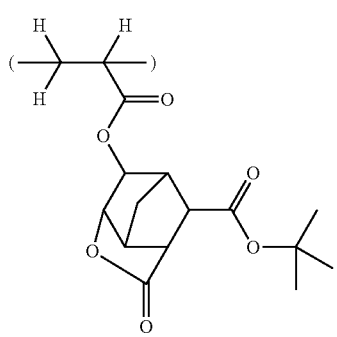
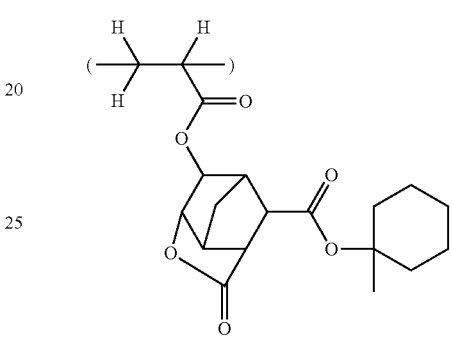
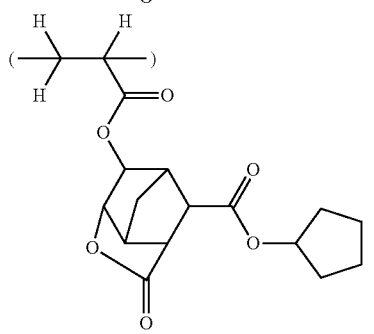
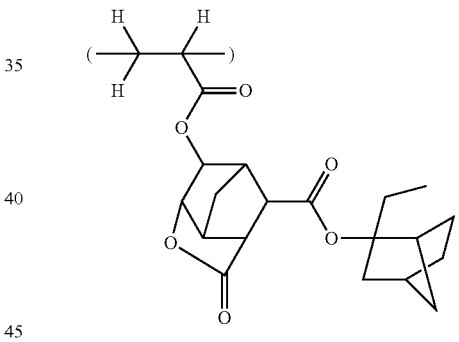
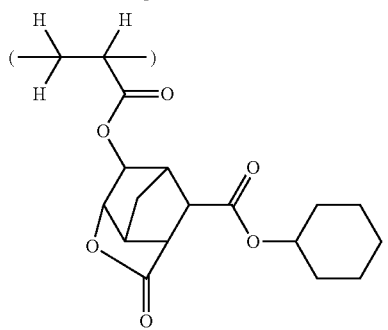
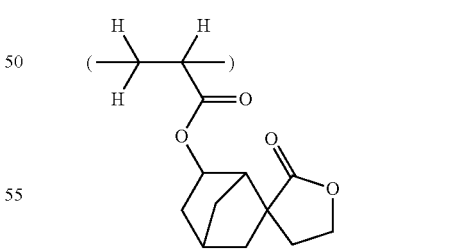
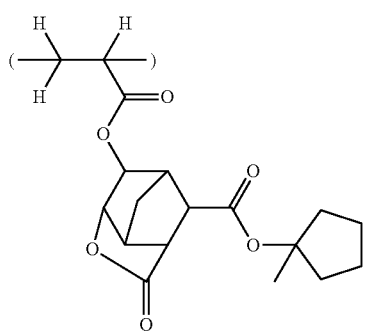
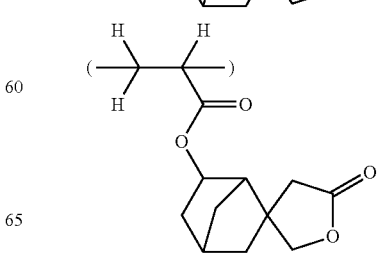

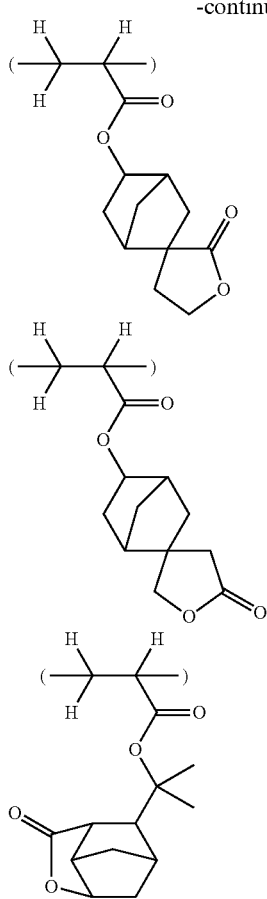
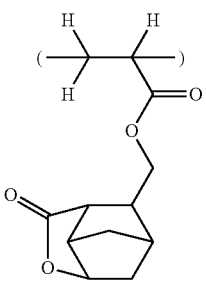
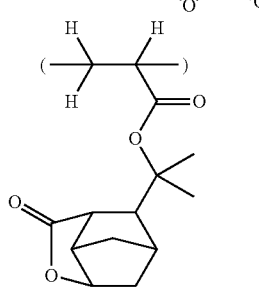
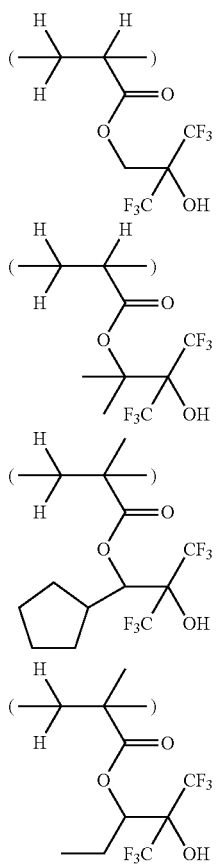
Especially, a repeating unit shown by the following general formula (4) and/or a repeating unit shown by the following general formula (5) are preferable.
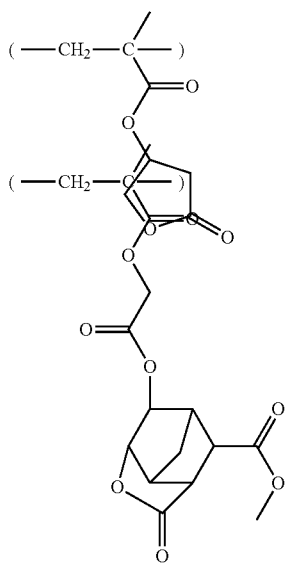
(4)
(5)
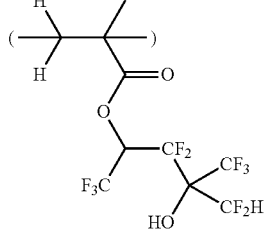
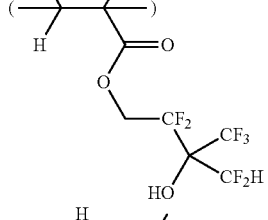
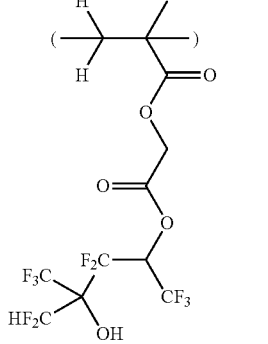
Illustrative example of the repeating unit having a hydroxyl group includes the followings.

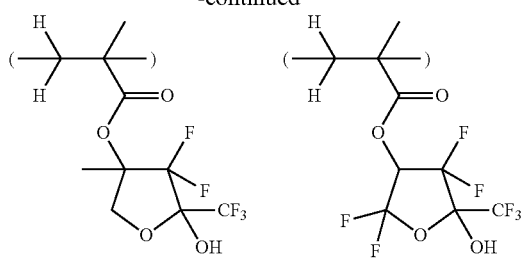
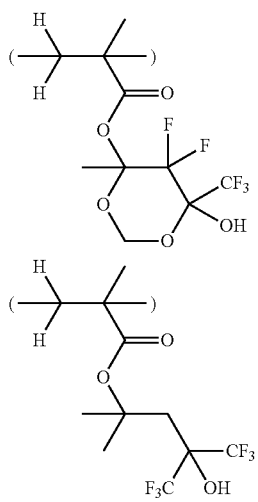
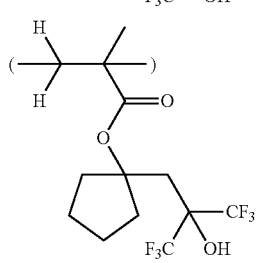
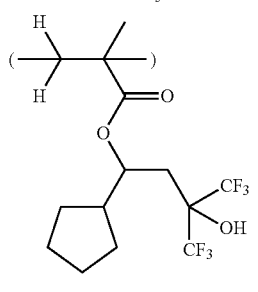
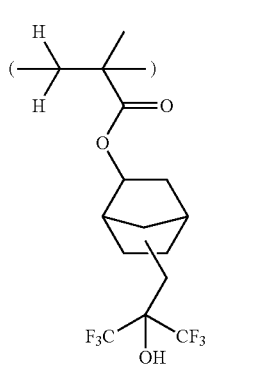
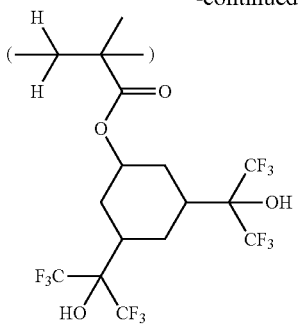
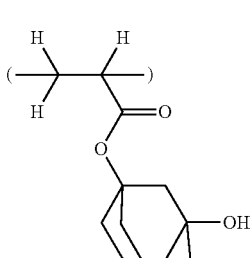
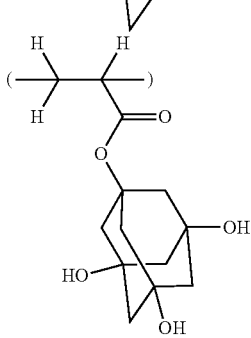
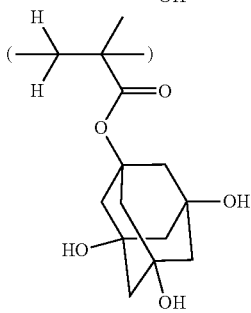
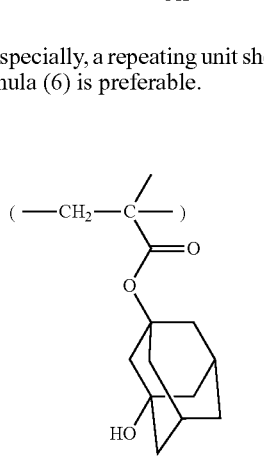
Especially, a repeating unit shown by the following general formula (6) is preferable.
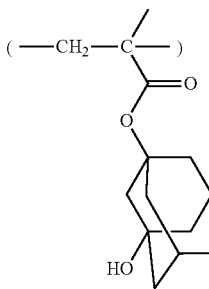

The resin of the component (A) of the positive resist composition of the present invention may optionally contain further a repeating unit other than the repeating units shown by the general formulae (1) and (2) and the repeating unit containing a hydroxyl group and/or a lactone ring; illustrative example thereof includes a repeating unit containing a carboxyl group or a fluoroalkyl group.

However, amount of the repeating unit containing a carboxyl group is preferably 10% or less by mol relative to total repeating units contained therein. If the amount is within this range, there are no fears of deterioration of pattern rectangularity and deterioration of resistance to pattern fall caused by swelling; and in addition, dissolution rate can be effectively controlled in a certain case.

In addition, a unit having a bridging cyclic structure may be contained therein. If amount of this unit is less than 10% by mol relative to total repeating units, pattern fall caused during development can be avoided with more surely and there is no fear of deterioration of LWR; and thus, this amount is preferable.

Specific examples of the unit having a carboxyl group or a fluoroalkyl group and the unit having a bridging cyclic structure are shown below, though not limited to them.

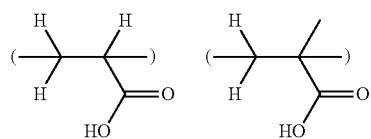

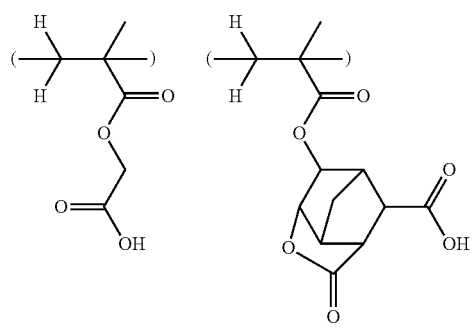

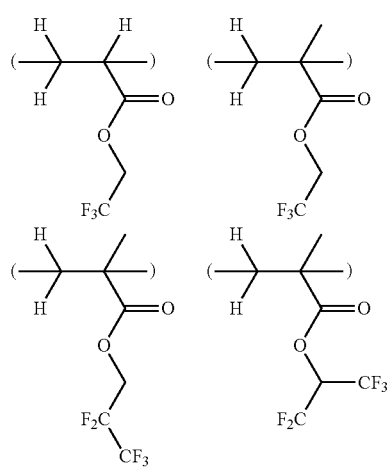

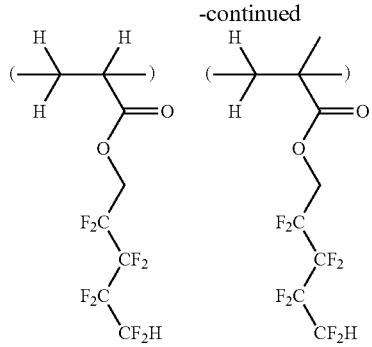

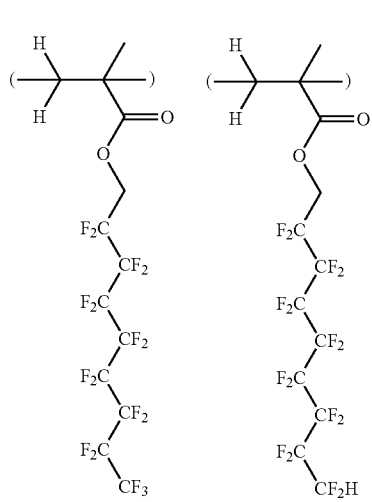

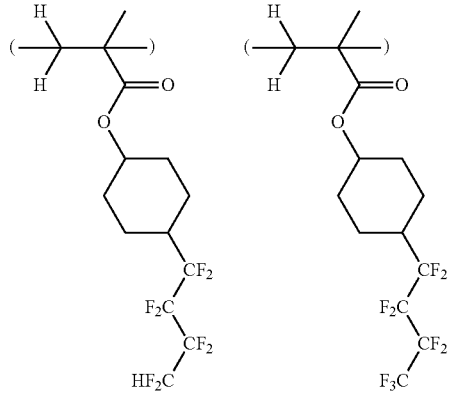

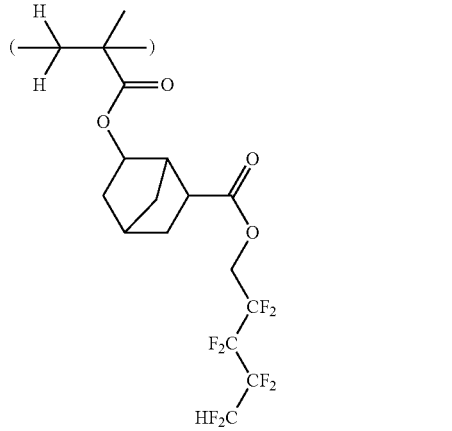

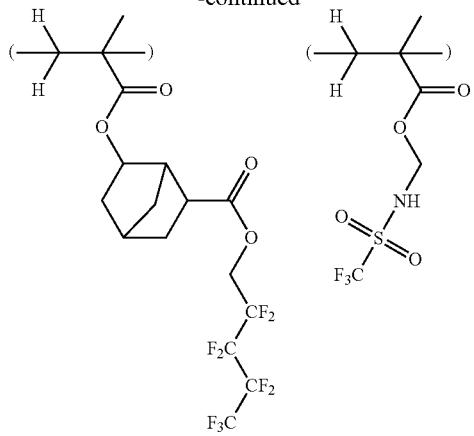

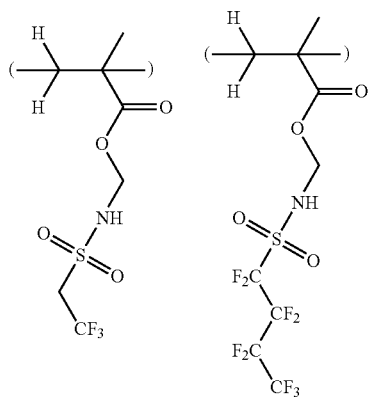

In the case that the resin of the component (A) is synthesized, polymerizable monomers corresponding to the repeating units shown by the general formulae (1) and (2), which are essential repeating units, and the repeating units shown by the general formulae (4) to (6), which are optional repeating units, are mixed, and then they are polymerized by adding an initiator and a chain-transfer agent.

Concerning the composition ratio among the respective repeating units constituting the resin (A) contained in the positive resist composition of the present invention, preferable is a composition ratio satisfying the following conditions, assuming that: "a" mol % represents a total content ratio of the repeating unit represented by the above general formula (1); "b" mol % represents a total content ratio of the repeating unit represented by the above formula (2); "c" mol % represents a total content ratio of the repeating unit containing a hydroxyl group; and "d" mol % represents a total content ratio of the repeating unit containing a lactone ring;

$a+b+c+d=100$, $0<a \le 50$, $10b<60$, and $20 \le d \le 70$, particularly, $a+b+c+d=100$, $0<a \le 40$, $10 \le b \le 60$, $0 \le c \le 30$, and $20 \le d \le 60$.

Concerning the molecular weight of the resin (A) contained in the positive resist composition of the present invention, excessively smaller weight-average molecular weights (Mw) lead to susceptibility of dissolution of the resin in water, while excessively larger weight-average molecular weights cause deterioration of solubility of the resin in alkali, coating defects upon spin coating thereof, and the like, with a great possibility. From that standpoint, it is preferable that the resin has a weight-average molecular weight of 1,000 to 500,000, preferably 2,000 to 30,000 as determined relative to polystyrene standards in gel permeation chromatography (GPC).

The positive resist composition of the present invention contains a photoacid generator as the component (B). This photoacid generator is not particularly restricted; and for example, those described in the Japanese Patent Laid-Open Publication No. 2011-95662 may be used.

Meanwhile, illustrative example of the photoacid generator preferably used in the positive resist composition of the present invention includes a sulfonium salt, bissulfonyl diazomethane, and N-sulfonyl oxyimide. The photoacid generator may be used singly or as a mixture of two or more kinds.

Amount of the component (B) is preferably in the range of 0.5 to 25 parts by mass relative to 100 parts by mass of the resin of the component (A).

The positive resist composition of the present invention contains a compound shown by the following general formula (3) as the component (C),

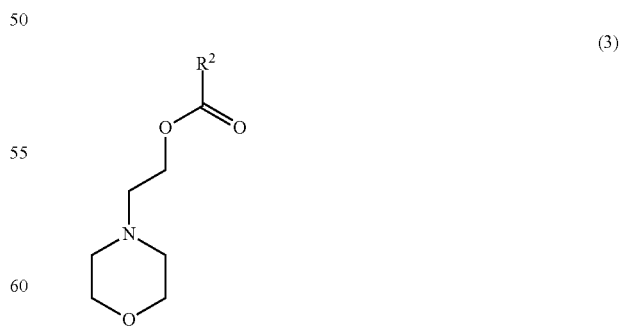

(3)

wherein $R^2$ represents a linear or a branched alkyl group having 10 to 20 carbon atoms and optionally containing an ether bond and an ester bond.

In particular, preferable of the component (C) is a compound containing a linear R² having 10 to 20 carbon atoms, or more preferable are the compounds having the following structures.

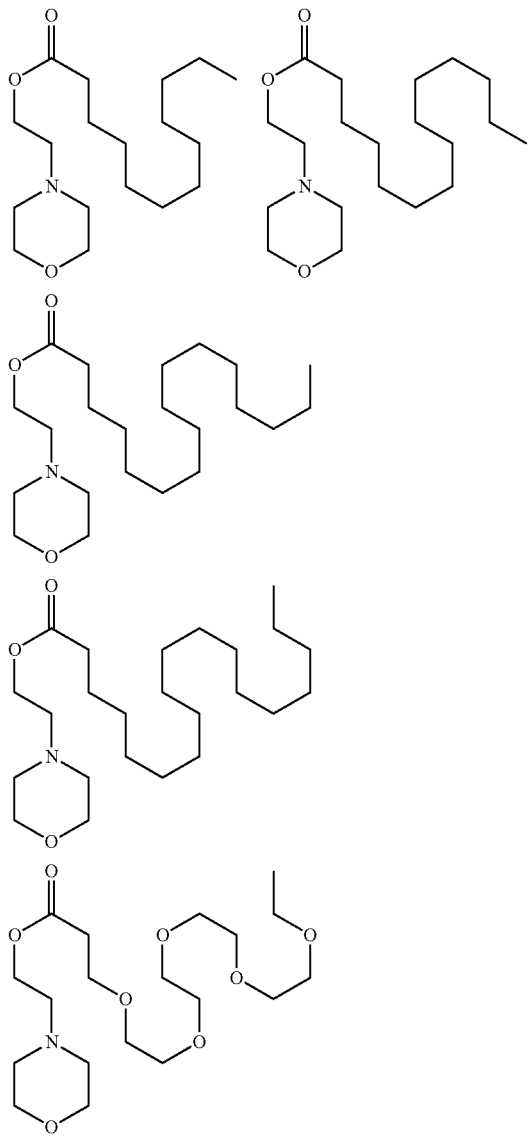

Amount of the component (C) is preferably in the range of 0.5 to 10 parts by mass relative to 100 parts by mass of the resin of the component (A). If the amount of the component (C) is within this range, effects of the present invention as mentioned above can be fully expressed; and thus, this amount is preferable.

The positive resist composition of the present invention contains following solvents as the component (D).

Usable as the solvent (D) is any organic solvent in so far as the same allows dissolution therein of the resin of the component (A), the photoacid generator of the component (B), the compound of the component (C), other additive(s), and the like. Inclusion of the organic solvent enables to exemplarily improve a coatability of the positive resist composition onto a substrate or the like. Examples of such an organic solvent include: ketones such as cyclohexanone, methyl-2-n-amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone; and these solvents may be used solely in one kind, or mixedly in two or more kinds, without limited thereto. To be preferably used in the present invention among these organic solvents, are diethylene glycol dimethyl ether, 1-ethoxy-2-propanol, propylene glycol monomethyl ether acetate, and mixed solvents thereof, which solvents are most excellent in solubility therein of the acid generator in the resist components.

Amount of the solvent of the component (D) is preferably in the range of 200 to 5000 parts by mass, in particular 400 to 4000 parts by mass, relative to 100 parts by mass of the base resin in the positive resist composition.

In addition, a compound generating an acid by acidic decomposition (acid-proliferating compound) may be added into the positive resist composition of the present invention. These compounds may be referred to the Japanese Patent Laid-Open Publication No. 2009-269953.

In the resist composition of the present invention, adding amount of the acid-proliferating compound is 2 or less parts by mass, or preferably 1 or less part by mass, relative to 100 parts by mass of the base resin in the resist composition. If the amount is 2 or less parts by mass, there are no fears of difficulty in control of acid diffusion, deterioration of resolution, and deterioration of a pattern profile; and thus, this amount is preferable.

In addition, a compound (solubility-controlling agent), having weight-average molecular weight of 3000 or less, whose solubility into an alkaline developer changes by action of an acid or by an organic acid derivative, may be added into the positive resist composition of the present invention; these compounds may be referred to the Japanese Patent Laid-Open Publication No. 2009-269953, similarly to the respective components mentioned above. By blending the solubility-controlling agent, difference in dissolution rates between the exposed part and the unexposed part can be made further larger so that resolution power can be improved further.

Separately from the foregoing component (C), a basic compound may also be added into the positive resist composition of the present invention. By blending a basic compound, resolution power can be improved further. Illustrative example of the basic compound includes primary, secondary, and tertiary amines described in the paragraphs [0146] to [0164] of the Japanese Patent Laid-Open Publication No. 2008-111103, especially an amine compound containing a hydroxyl group, an ether group, an ester group, a lactone ring, a cyano group, or a sulfonate ester group, and a compound containing a carbamate group described in the Japanese Patent Laid-Open Publication No. 2001-166476; and adding amount thereof is preferably 0 to 4 parts by mass relative to 100 parts by mass of the base resin.

A surfactant component may be added into the positive resist composition of the present invention, while the surfactant component is not particularly restricted; for example, those alkaline-soluble surfactants described in the Japanese Patent Laid-Open Publication No. 2008-122932 may be used. By adding the surfactant, coating properties of the resist composition may be further improved or controlled better.

In addition, the surfactant may be used as a mixture thereof; total adding amount thereof is 0.001 to 20 parts by mass, or preferably 0.01 to 10 parts by mass, relative to 100 parts by mass of the base resin of the resist composition.

The positive resist composition as mentioned above can give excellent resolution and pattern profile as mentioned above in a lithography technology (including a multilayer resist method) even in the case of usual pattern exposure, development, and so on, though this is extremely useful in an immersion lithography using a formed top coat thereon whereby photo-exposure is done through water.

The present invention provides a patterning process, wherein the process comprises:

a step of applying on a substrate a positive resist composition comprising (A) a resin having repeating units shown by the following general formulae (1) and (2) as repeating units that contain acid labile groups and being capable of increasing its alkaline solubility by an acid, (B) a photoacid generator, (C) a compound shown by the following general formula (3), and (D) a solvent, and then heating the composition to form a photoresist film, a step of forming a top coat on the photoresist film, a step of immersion exposure thereof through water by using a high energy beam having a wavelength ranging from 180 to 250 nm, and a step of development by using an alkaline developer.

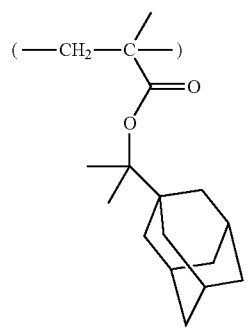

(1)

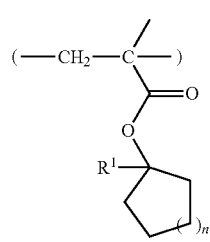

(2)

wherein $R^1$ represents a linear or a branched alkyl group having 1 to 10 carbon atoms and "n" represents an integer of 1 to 3;

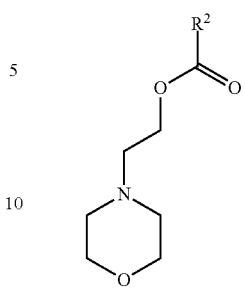

(3)

wherein $R^2$ represents a linear or a branched alkyl group having 10 to 20 carbon atoms and optionally containing an ether bond and an ester bond.

Hereinafter, the patterning process of the present invention will be explained in detail.

Patterning using the positive resist composition of the present invention may be effected by using a heretofore known lithography technology. For example, the positive resist composition is applied onto a substrate for manufacturing of an integrated circuit (Si $SiO_2$, SiN, SiON, TIN, WSi, BPSG, SOG, substrate coated with an organic anti-reflective film, and so on) or a substrate for manufacturing of a mask circuit (Cr, CrO, CrON, MoSi, and so on) by such a method as a spin coating method so as to give a film thickness of 0.05 to 2.0 μm, and then this is subjected to a heat-treatment (prebake) on a hot plate at 60 to 150° C. for 1 to 10 minutes, or preferably at 80 to 140° C. for 1 to 5 minutes to form a photoresist film.

Then, a top coat not soluble in water is formed on the photoresist film thus obtained.

The top coat not soluble in water used to protect elution from the photoresist film and to increase water repellent property of the film surface, may be classified into roughly two kinds. One is an organic-solvent-removal type wherein the top coat needs to be removed before alkaline development by using an organic solvent not dissolving the photoresist film; and the other is an alkaline-soluble type wherein the top coat soluble in an alkaline developer is removed simultaneously with removal of a soluble resist part.

In the latter case, a material containing a base polymer, not soluble in water but soluble in an alkaline developer, especially having a 1,1,1,3,3,3-hexafluoro-2-propanol residue, dissolved in an alcohol solvent having 4 or more carbon atoms, an ether solvent having 8 to 12 carbon atoms, or a mixture of these solvents, is preferable. In addition, a material containing the foregoing surfactant, not soluble in water but soluble in an alkaline developer, dissolved in an alcohol solvent having 4 or more carbon atoms, an ether solvent having 8 to 12 carbon atoms, or a mixture of these solvents, may also be used.

As a measure for the patterning process, after formation of a photoresist film, an acid generator and so on may be extracted from the film surface by rinsing with pure water (post-soak) or a particle may be flushed away; or water remained on the film after exposure may be removed by rinsing (post-soak).

Then, with covering over the resist film thus formed by a mask to form an intended pattern, an immersion exposure is carried out by using a high energy beam having wavelength of 180 to 250 nm, such as a far UV beam and an excimer laser beam, through water between the mask and the substrate (immersion method). The irradiation is made thereonto with the exposure dose of preferably 1 to 200 mJ/cm$^2$, or in particular 10 to 100 mJ/cm$^2$. The positive resist composition of the present invention is most suitably applied to fine patterning using a far UV beam or an excimer laser beam having wavelength of 180 to 250 nm as mentioned above.

Thereafter, post-exposure bake (PEB) is done on a hot plate at 60 to 150° C. for 1 to 5 minutes, or preferably at 80 to 140° C. for 1 to 3 minutes. Then, development is done by using an aqueous alkaline developer such as tetramethyl ammonium hydroxide (TMAH) with concentration thereof being 0.1 to 5% by mass, or preferably 2 to 3% by mass, for 0.1 to 3 minutes, or preferably for 0.5 to 2 minutes, with a usually used method such as a dip method, a puddle method, and a spray method to form an intended pattern on a substrate.

EXAMPLES

Hereinafter embodiments of the present invention will be explained specifically by showing Examples and Comparative Examples. However the present invention is not restricted by these descriptions.

Composition ratio (mol ratio) of the repeating units that constitute the resins used in the present evaluation as well as molecular weights (Mw) of the resins thereof are shown in Table 1. Meanwhile, molecular weight (Mw) is expressed by the polystyrene-equivalent weight-average molecular weight measured with a GPC method. Structures of each repeating unit are shown in Table 2. The resins P-01 to P-09 among the resins shown in Table 1 correspond to the resins of the component (A), the essential component in the positive resist composition of the present invention.

TABLE 1

| Resin | Unit1 | (mol ratio) | Unit2 | (mol ratio) | Unit3 | (mol ratio) | Unit4 | (mol ratio) | Unit5 | (mol ratio) | Mw |
|---|---|---|---|---|---|---|---|---|---|---|---|
| P-01 | A-6 | (0.20) | A-4 | (0.10) | A-7 | (0.25) | B-3 | (0.35) | B-4 | (0.10) | 7,500 |
| P-02 | A-6 | (0.20) | A-5 | (0.10) | A-7 | (0.25) | B-3 | (0.35) | B-4 | (0.10) | 7,100 |
| P-03 | A-6 | (0.20) | A-1 | (0.10) | A-7 | (0.25) | B-2 | (0.35) | B-5 | (0.10) | 7,400 |
| P-04 | A-6 | (0.20) | A-2 | (0.10) | A-7 | (0.25) | B-2 | (0.35) | B-5 | (0.10) | 8,200 |
| P-05 | A-6 | (0.15) | A-3 | (0.15) | A-7 | (0.20) | B-2 | (0.40) | B-5 | (0.10) | 7,500 |
| P-06 | A-6 | (0.20) | A-1 | (0.10) | A-7 | (0.25) | B-3 | (0.35) | B-5 | (0.10) | 7,100 |
| P-07 | A-6 | (0.20) | A-2 | (0.10) | A-7 | (0.25) | B-3 | (0.35) | B-5 | (0.10) | 8,800 |
| P-08 | A-6 | (0.20) | A-3 | (0.20) | A-7 | (0.25) | B-3 | (0.35) | | | 8,000 |
| P-09 | A-6 | (0.30) | A-3 | (0.30) | B-2 | (0.40) | | | | | 9,100 |
| P-10 | A-6 | (0.40) | A-7 | (0.20) | B-4 | (0.40) | | | | | 9,200 |
| P-11 | A-6 | (0.40) | A-7 | (0.20) | B-3 | (0.40) | | | | | 7,000 |
| P-12 | A-1 | (0.40) | A-7 | (0.15) | B-1 | (0.45) | | | | | 7,400 |
| P-13 | A-2 | (0.40) | A-7 | (0.15) | B-1 | (0.45) | | | | | 7,100 |
| P-14 | A-3 | (0.40) | A-7 | (0.15) | B-1 | (0.45) | | | | | 8,200 |
| P-15 | A-4 | (0.40) | A-7 | (0.15) | B-1 | (0.45) | | | | | 8,700 |
| P-16 | A-5 | (0.40) | A-7 | (0.15) | B-1 | (0.45) | | | | | 7,600 |

TABLE 2
| | |
|---|---|
| 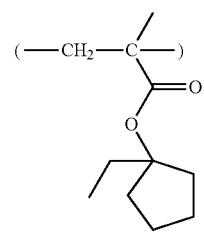 A-1 | 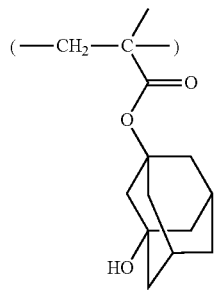 A-7 |
| 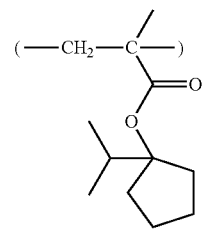 A-2 | 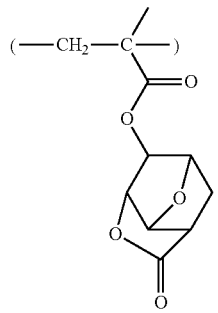 B-1 |
| 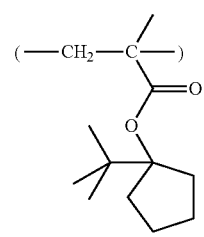 A-3 | 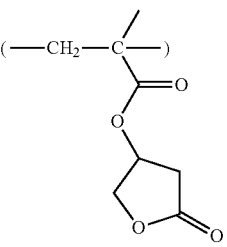 B-2 |
| 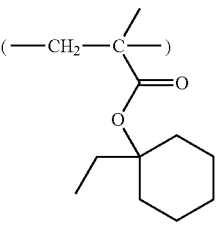 A-4 | 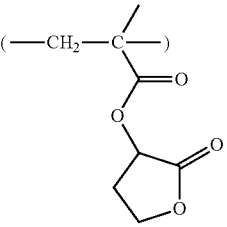 B-3 |
| 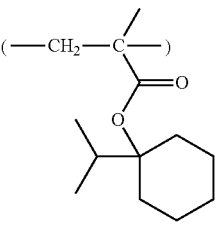 A-5 | 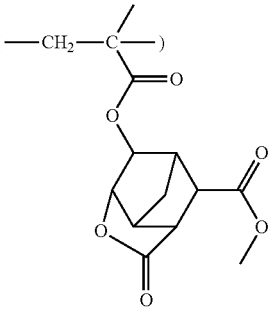 B-4 |
| 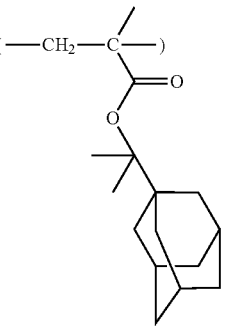 A-6 | |

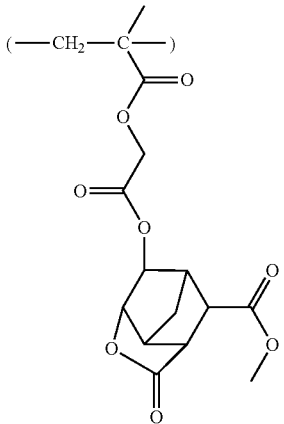

B-5

Preparation of Resist Compositions

Then, in addition to the foregoing resins, various photoacid generators and various quenchers (basic compound) were dissolved in a solvent with the blending ratio (parts by mass) shown in Table 3; and then, each of the solutions thus obtained was filtrated through a filter (pore diameter of 0.2 μm) made of Teflon (registered trade mark) to obtain each resist composition. Structures of the acid generators and the basic compounds in Table 3 are shown in Table 4. The basic compounds Q1 to Q5 among the basic compounds shown in Table 4 correspond to the compounds of the component (C), the essential component in the positive resist composition of the present invention. That is, the resist compositions R-01 to R09 and R-17 to R20 among the compositions shown in Table 3 correspond to the positive resist compositions of the present invention. The compositions R-10 to R-16 and R-21 to R-25 are the comparative resist compositions.

TABLE 3

| Resist | Resin | Acid generator | Basic compound | Solvent 1 | Solvent 2 |
| --- | --- | --- | --- | --- | --- |
| R-01 | P-01 (80) | PAG-1 (9.6) PAG-2 (5.1) | Q3 (2.3) | PGMEA (1428.0) | CyHO (612.0) |
| R-02 | P-02 (80) | PAG-1 (13.8) | Q3 (2.3) | PGMEA (1428.0) | CyHO (612.0) |
| R-03 | P-03 (80) | PAG-1 (13.8) | Q1 (2.0) | PGMEA (1428.0) | CyHO (612.0) |
| R-04 | P-04 (80) | PAG-1 (13.8) | Q4 (2.5) | PGMEA (1428.0) | CyHO (612.0) |
| R-05 | P-05 (80) | PAG-1 (9.6) PAG-2 (5.1) | Q4 (2.5) | PGMEA (1428.0) | CyHO (612.0) |
| R-06 | P-06 (80) | PAG-1 (13.8) | Q4 (2.5) | PGMEA (1428.0) | CyHO (612.0) |
| R-07 | P-07 (80) | PAG-1 (13.8) | Q4 (2.5) | PGMEA (1428.0) | CyHO (612.0) |
| R-08 | P-08 (80) | PAG-1 (13.8) | Q4 (2.5) | PGMEA (1428.0) | CyHO (612.0) |
| R-09 | P-09 (80) | PAG-1 (13.8) | Q2 (2.2) | PGMEA (1428.0) | CyHO (612.0) |
| R-10 | P-10 (80) | PAG-1 (13.8) | Q2 (2.2) | PGMEA (1428.0) | CyHO (612.0) |
| R-11 | P-11 (80) | PAG-1 (13.8) | Q2 (2.2) | PGMEA (1428.0) | CyHO (612.0) |
| R-12 | P-12 (80) | PAG-1 (13.8) | Q2 (2.2) | PGMEA (1428.0) | CyHO (612.0) |
| R-13 | P-13 (80) | PAG-1 (13.8) | Q2 (2.2) | PGMEA (1428.0) | CyHO (612.0) |
| R-14 | P-14 (80) | PAG-1 (13.8) | Q4 (2.5) | PGMEA (1428.0) | CyHO (612.0) |
| R-15 | P-15 (80) | PAG-1 (13.8) | Q5 (2.6) | PGMEA (1428.0) | CyHO (612.0) |
| R-16 | P-16 (80) | PAG-1 (13.8) | Q5 (2.6) | PGMEA (1428.0) | CyHO (612.0) |
| R-17 | P-01 (80) | PAG-1 (13.8) | Q1 (2.0) | PGMEA (1428.0) | CyHO (612.0) |
| R-18 | P-01 (80) | PAG-1 (13.8) | Q2 (2.2) | PGMEA (1428.0) | CyHO (612.0) |
| R-19 | P-01 (80) | PAG-1 (13.8) | Q3 (2.3) | PGMEA (1428.0) | CyHO (612.0) |
| R-20 | P-01 (80) | PAG-1 (13.8) | Q4 (2.5) | PGMEA (1428.0) | CyHO (612.0) |
| R-21 | P-05 (80) | PAG-1 (13.8) | Q6 (1.6) | PGMEA (1428.0) | CyHO (612.0) |
| R-22 | P-05 (80) | PAG-1 (9.6) PAG-2 (5.1) | Q6 (1.6) | PGMEA (1428.0) | CyHO (612.0) |
| R-23 | P-05 (80) | PAG-1 (13.8) | Q7 (1.5) | PGMEA (1428.0) | CyHO (612.0) |
| R-24 | P-04 (80) | PAG-1 (13.8) | Q8 (1.2) | PGMEA (1428.0) | CyHO (612.0) |
| R-25 | P-04 (80) | PAG-1 (13.8) | Q9 (1.1) | PGMEA (1428.0) | CyHO (612.0) |

TABLE 4
| | |
|---|---|
| 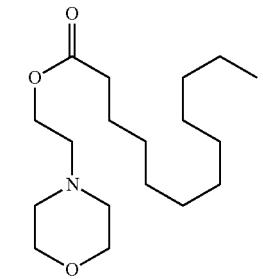 [SMILES: CCCCCCCCCCCC(=O)OCCN1CCOCC1] Q-1 | 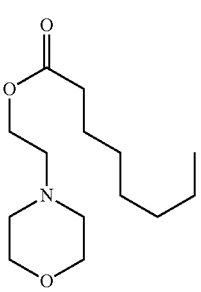 Q-6 |
| 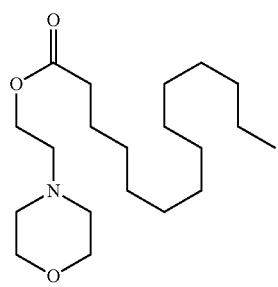 [SMILES: CCCCCCCCCCCCCC(=O)OCCN1CCOCC1] Q-2 | 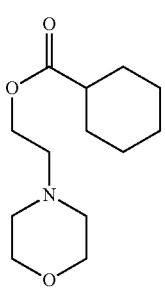 [SMILES: O=C(OCCN1CCOCC1)C1CCCCC1] Q-7 |
| 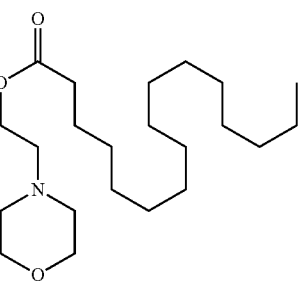 Q-3 | 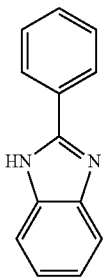 Q-8 |
| 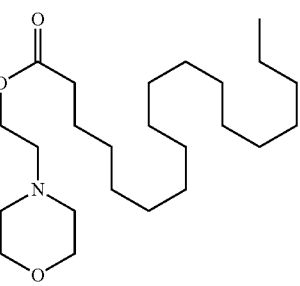 Q-4 | 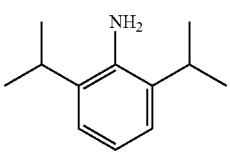 Q-9 |
| 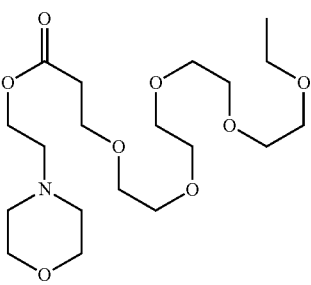 Q-5 | 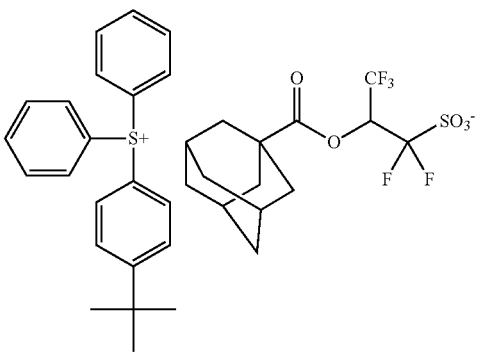 PAG-1 |

TABLE 4-continued

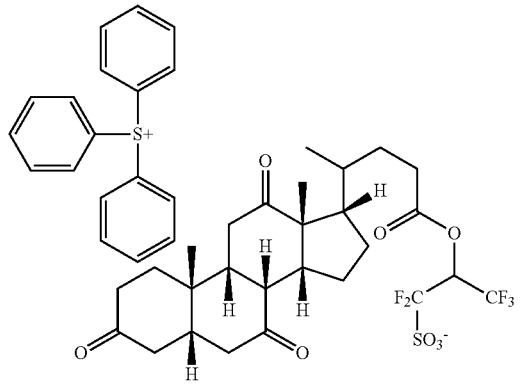

PAG-2

Solvents shown in Table 3 are as follows.

PGMEA: Propylene glycol monomethyl ether acetate

CyHO: Cyclohexanone

Preparation of Resist Top Coats

A base polymer (TC Polymer-1 and TC Polymer-2) and an organic solvent were mixed with the composition shown below; and then, the resulting solution after dissolution was filtrated through a filter (pore diameter of 0.2 μm) made of Teflon (registered trade mark) to obtain a top coat material (TC-1 and TC-2).

TC-1:
Composition of the Mixture: 100 parts by mass of TC Polymer-1 shown by the following formula, 2600 parts by mass of Organic Solvent-1, and 260 parts by mass of Organic Solvent-2

TC-2:
Composition of the Mixture: 100 parts by mass of TC Polymer-2 shown by the following formula, 2600 parts by mass of Organic Solvent-1, and 260 parts by mass of Organic Solvent-2

TC Polymers (see the following structures)
TC Polymer-1 (molecular weight of 7500)

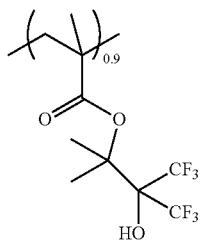 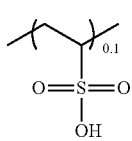

TC Polymer-2 (molecular weight of 8200)

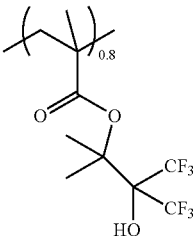 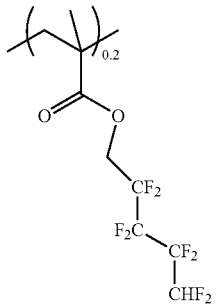

Organic Solvent-1: isoamyl ether
Organic Solvent-2: 2-methyl-1-butanol

Evaluation Method

Examples 1 to 13 and Comparative Examples 1 to 12

An anti-reflective film solution (ARC-29A, manufactured by Nissan Chemical Industries, Ltd.) was applied onto a silicon substrate, and then it was baked at 200° C. for 60 seconds to obtain an anti-reflective film (film thickness of 100 nm); onto this was applied a resist solution (R-01 to R-25) by a spin coating method; and then, it was baked on a hot plate at 100° C. for 60 seconds to obtain a photoresist film having a film thickness of 100 nm.

Onto this was applied a resist top coat material (TC-1 and TC-2); and then, it was baked at 100° C. for 60 seconds to obtain a top coat having a film thickness of 50 nm. This was immersion-exposed by using an ArF excimer laser scanner (NSR-S610C: manufactured by Nikon Corp., NA=1.30, σ 0.85, ¾ annular illumination, 6% half tone phase shift mask), baked at an arbitrary temperature (shown in Tables 5 and 6) for 60 seconds (PEB), and then developed by an aqueous tetramethyl ammonium hydroxide solution with concentration of 2.38% by mass for 60 seconds to form a pattern.

Evaluation of the resist was made as to the pattern with a 70 nm line and a 150 nm pitch; and the optimum exposure dose (Eop, mJ/cm$^2$) was taken when the line width of 45 nm was obtained by an electron microscope. Pattern profiles were compared on the basis of the pattern cross section results observed at that time. The focal point at the optimum exposure dose was moved up and down whereby range of the focal point to resolve the trench pattern with the target size of 45 nm±10% (namely 41 to 50 nm) was obtained; and this was taken as DOF1 (nm). Larger this value, better the performance with wider margin of misalignment in the focal point. Further, the pattern with a 65 nm trench and a 160 nm pitch was also observed whereby range of the focal point to resolve with the target size of 45 nm±10% (namely 41 to 50 nm) at the exposure dose to give a 45 nm trench and a 160 nm pitch was obtained; and this was taken as DOF2 (nm). Evaluation results (Examples 1 to 13) of the resist compositions of the present invention shown in the above Table (R-01 to R-09 and R-17 to R-20) are shown in Table 5. Evaluation results (Comparative Examples 1 to 12) of the comparative resist compositions (R-10 to R-16 and R-21 to R-25) are shown in Table 6.

TABLE 5

| Example | Resist | Top coat | PEB | Optimum exposure dose (DOF1) | Optimum exposure dose (DOF2) | Pattern Profile | DOF1 (nm) | DOF2 (nm) |
|---|---|---|---|---|---|---|---|---|
| 01 | R-01 | TC-1 | 105° C. | 36.0 mJ/cm$^2$ | 32.0 mJ/cm$^2$ | Rectangular profile | 100 | 110 |
| 02 | R-02 | TC-1 | 105° C. | 33.0 mJ/cm$^2$ | 30.0 mJ/cm$^2$ | Rectangular profile | 115 | 105 |
| 03 | R-03 | TC-1 | 100° C. | 34.0 mJ/cm$^2$ | 30.0 mJ/cm$^2$ | Rectangular profile | 105 | 105 |
| 04 | R-04 | TC-1 | 95° C. | 35.0 mJ/cm$^2$ | 31.0 mJ/cm$^2$ | Rectangular profile | 120 | 125 |
| 05 | R-05 | TC-1 | 95° C. | 33.0 mJ/cm$^2$ | 30.0 mJ/cm$^2$ | Rectangular profile | 130 | 125 |
| 06 | R-06 | TC-1 | 100° C. | 33.0 mJ/cm$^2$ | 28.0 mJ/cm$^2$ | Rectangular profile | 125 | 120 |
| 07 | R-07 | TC-1 | 100° C. | 34.0 mJ/cm$^2$ | 29.0 mJ/cm$^2$ | Rectangular profile | 110 | 110 |
| 08 | R-08 | TC-1 | 100° C. | 35.0 mJ/cm$^2$ | 31.0 mJ/cm$^2$ | Rectangular profile | 115 | 110 |
| 09 | R-09 | TC-1 | 90° C. | 38.0 mJ/cm$^2$ | 33.0 mJ/cm$^2$ | Rectangular profile | 120 | 100 |
| 10 | R-17 | TC-2 | 100° C. | 32.0 mJ/cm$^2$ | 29.0 mJ/cm$^2$ | Rectangular profile | 105 | 115 |
| 11 | R-18 | TC-2 | 100° C. | 33.0 mJ/cm$^2$ | 30.0 mJ/cm$^2$ | Rectangular profile | 110 | 130 |
| 12 | R-19 | TC-2 | 100° C. | 35.0 mJ/cm$^2$ | 31.0 mJ/cm$^2$ | Rectangular profile | 110 | 130 |
| 13 | R-20 | TC-2 | 100° C. | 37.0 mJ/cm$^2$ | 34.0 mJ/cm$^2$ | Rectangular profile | 120 | 130 |

TABLE 6

| Comparative Example | Resist | Top coat | PEB | Optimum exposure dose (DOF1) | Optimum exposure dose (DOF2) | Pattern Profile | DOF1 (nm) | DOF2 (nm) |
|---|---|---|---|---|---|---|---|---|
| 01 | R-10 | TC-1 | 110° C. | 35.0 mJ/cm$^2$ | 31.0 mJ/cm$^2$ | Rectangular profile | 125 | 85 |
| 02 | R-11 | TC-1 | 100° C. | 43.0 mJ/cm$^2$ | 29.0 mJ/cm$^2$ | Rectangular profile | 120 | 85 |
| 03 | R-12 | TC-1 | 100° C. | 28.0 mJ/cm$^2$ | 25.0 mJ/cm$^2$ | Slightly rounding profile | 70 | 135 |
| 04 | R-13 | TC-1 | 95° C. | 29.0 mJ/cm$^2$ | 26.0 mJ/cm$^2$ | Slightly rounding profile | 70 | 135 |
| 05 | R-14 | TC-1 | 95° C. | 30.0 mJ/cm$^2$ | 27.0 mJ/cm$^2$ | Slightly rounding profile | 80 | 105 |
| 06 | R-15 | TC-1 | 100° C. | 35.0 mJ/cm$^2$ | 32.0 mJ/cm$^2$ | Slightly rounding profile | 75 | 110 |
| 07 | R-16 | TC-1 | 95° C. | 36.0 mJ/cm$^2$ | 32.0 mJ/cm$^2$ | Slightly rounding profile | 75 | 110 |
| 08 | R-21 | TC-1 | 95° C. | 28.0 mJ/cm$^2$ | 25.0 mJ/cm$^2$ | Rounding profile | 45 | 55 |
| 09 | R-22 | TC-1 | 95° C. | 34.0 mJ/cm$^2$ | 31.0 mJ/cm$^2$ | Rounding profile | 55 | 65 |
| 10 | R-23 | TC-1 | 95° C. | 41.0 mJ/cm$^2$ | 37.0 mJ/cm$^2$ | Rounding profile | 60 | 65 |
| 11 | R-24 | TC-1 | 95° C. | 30.0 mJ/cm$^2$ | 27.0 mJ/cm$^2$ | Rounding profile | 55 | 70 |
| 12 | R-25 | TC-1 | 95° C. | 33.0 mJ/cm$^2$ | 28.0 mJ/cm$^2$ | Rounding profile | 30 | 45 |

From the results shown in Table 5 and Table 6, it became clear that excellent pattern profile and DOF characteristics could be obtained with the positive resist compositions of the present invention.

The present invention is not limited to the embodiment described above. The above-described aspects are mere examples and those having substantially the same structure as technical ideas described in the appended claims and providing the similar functions and advantages are included in the scope of the present invention.

What is claimed is:

1. A positive resist composition comprising:
(A) a resin having repeating units shown by the following general formula (1) and general formula (2) as repeating units that contain acid labile groups and being capable of increasing its alkaline solubility by an acid:

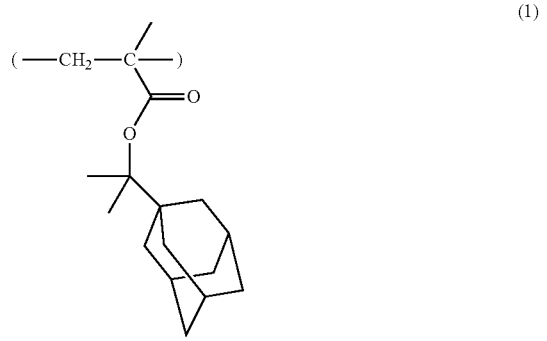

-continued

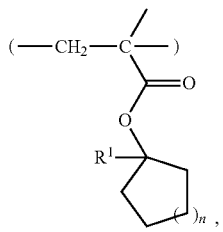
(2)

where:
R¹ represents a linear or a branched alkyl group having 1 to 10 carbon atoms; and
"n" represents an integer of 1 to 3;
(B) a photoacid generator,
(C) a compound shown by the following general formula (3):

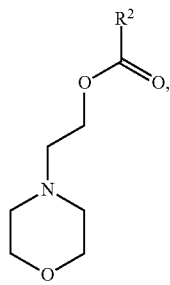
(3)

where R² represents a linear or a branched alkyl group having 10 to 20 carbon atoms and optionally containing an ether bond and an ester bond; and
(D) a solvent,
wherein the photoacid generator (B) is:
a sulfonium salt containing an anion represented by the following formula (7):

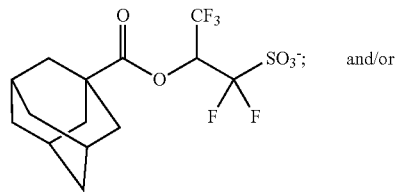
(7)

and/or a sulfonium salt containing an anion represented by the following formula (8):

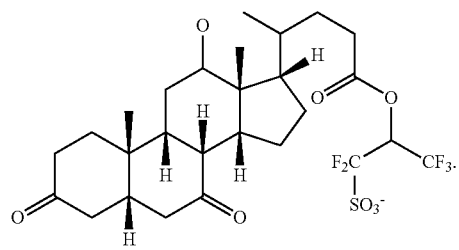
(8)

2. The positive resist composition according to claim 1, wherein the resin of the component (A) contains further:
a repeating unit shown by the following general formula (4):

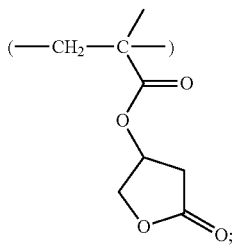
(4)

and/or a repeating unit shown by the following general formula (5):

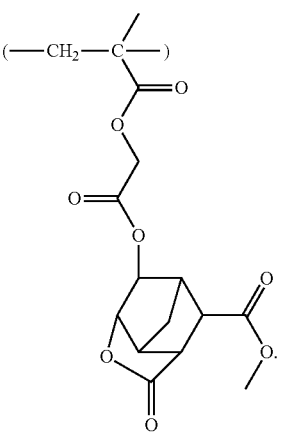
(5)

3. The positive resist composition according to claim 1, wherein the resin of the component (A) contains further a repeating unit shown by the following general formula (6):

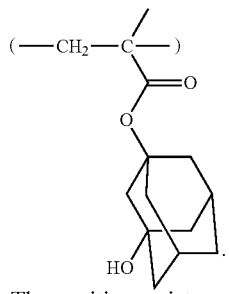
(6)

4. The positive resist composition according to claim 2, wherein the resin of the component (A) contains further a repeating unit shown by the following general formula (6):

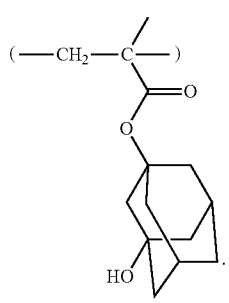
(6)

5. The positive resist composition according to claim 1, wherein amount of the component (C) is 0.5 to 10 parts by mass relative to 100 parts by mass of the resin of the component (A).

6. The positive resist composition according to claim 2, wherein amount of the component (C) is 0.5 to 10 parts by mass relative to 100 parts by mass of the resin of the component (A).

7. The positive resist composition according to claim 3, wherein amount of the component (C) is 0.5 to 10 parts by mass relative to 100 parts by mass of the resin of the component (A).

8. The positive resist composition according to claim 4, wherein amount of the component (C) is 0.5 to 10 parts by mass relative to 100 parts by mass of the resin of the component (A).

9. A patterning process, wherein the process comprises:

a step of applying on a substrate a positive resist composition comprising:

(A) a resin having repeating units shown by the following general formula (1) and general formula (2) as repeating units that contain acid labile groups and being capable of increasing its alkaline solubility by an acid:

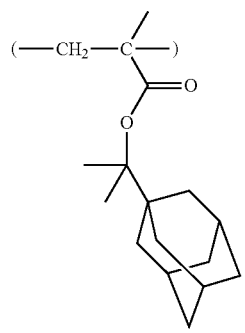

(1)

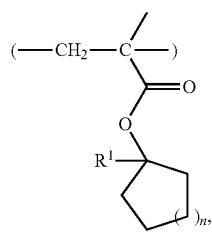

(2)

where:

$R^1$ represents a linear or a branched alkyl group having 1 to 10 carbon atoms, and "n" represents an integer of 1 to 3;

(B) a photoacid generator, (C) a compound shown by the following general formula (3):

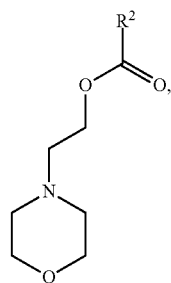

(3)

where $R^2$ represents a linear or a branched alkyl group having 10 to 20 carbon atoms and optionally containing an ether bond and an ester bond; and (D) a solvent, and then heating the composition to form a photoresist film, a step of forming a top coat on the photoresist film, a step of immersion exposure thereof through water by using a high energy beam having a wavelength ranging from 180 to 250 nm, and a step of development by using an alkaline developer, wherein the photoacid generator (B) is:

a sulfonium salt containing an anion represented by the following formula (7):

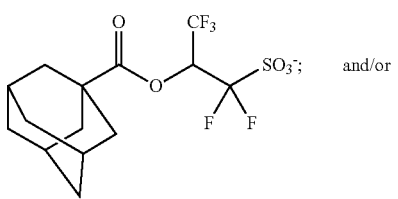

(7)

and/or a sulfonium salt containing an anion represented by the following formula (8):

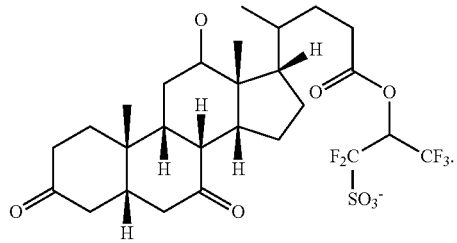

(8)

10. The patterning process according to claim 9, wherein the resin of the component (A) contains further:

a repeating unit shown by the following general formula (4):

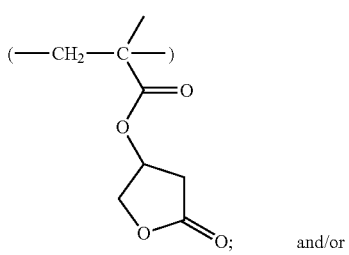

(4)

and/or a repeating unit shown by the following general formula (5):

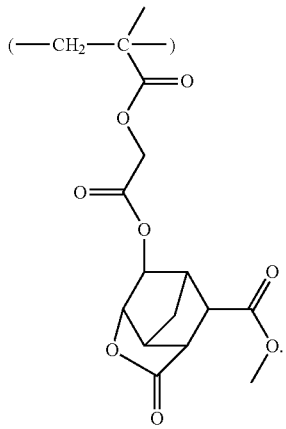
(5)

11. The patterning process according to claim 9, wherein the resin of the component (A) contains further a repeating unit shown by the following general formula (6):

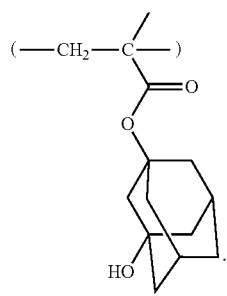
(6)

12. The patterning process according to claim 10, wherein the resin of the component (A) contains further a repeating unit shown by the following general formula (6):

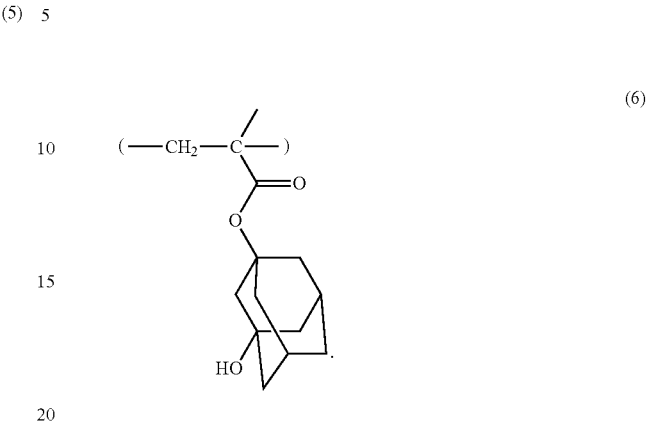
(6)

13. The patterning process according to claim 9, wherein amount of the component (C) is 0.5 to 10 parts by mass relative to 100 parts by mass of the resin of the component (A).

14. The patterning process according to claim 10, wherein amount of the component (C) is 0.5 to 10 parts by mass relative to 100 parts by mass of the resin of the component (A).

15. The patterning process according to claim 11, wherein amount of the component (C) is 0.5 to 10 parts by mass relative to 100 parts by mass of the resin of the component (A).

16. The patterning process according to claim 12, wherein amount of the component (C) is 0.5 to 10 parts by mass relative to 100 parts by mass of the resin of the component (A).

* * * * *